United States Patent [19]

Daniels et al.

[11] 4,421,850
[45] Dec. 20, 1983

[54] IMMOBILIZATION OF ENZYMES

[75] Inventors: Michael J. Daniels; Digby M. Farmer, both of Reading, England

[73] Assignee: Tate & Lyle Limited, United England

[21] Appl. No.: 237,637

[22] Filed: Feb. 24, 1981

[30] Foreign Application Priority Data

Feb. 26, 1980 [GB] United Kingdom ................. 8006448

[51] Int. Cl.³ .......................... C12P 1/00; C12P 19/20; C12N 11/00; C12N 11/02
[52] U.S. Cl. ....................................... 435/41; 435/96; 435/174; 435/177
[58] Field of Search ................ 435/174, 176, 177, 180, 435/181, 182, 41, 96

[56] References Cited

U.S. PATENT DOCUMENTS

| | | | |
|---|---|---|---|
| 3,796,634 | 3/1974 | Haynes et al. | 435/180 |
| 3,980,521 | 9/1976 | Amotz et al. | 435/174 |
| 4,004,979 | 1/1977 | Avrameas et al. | 435/181 X |
| 4,008,126 | 2/1977 | Keyes | 435/176 |
| 4,266,029 | 5/1981 | Branner-Jorgensen | 435/176 |
| 4,268,423 | 5/1981 | Rohrbach et al. | 435/180 X |

OTHER PUBLICATIONS

Zaborsky, O. R., Covalent Linkage: III Immobilization of Enzymes by Intermolecular Cross-Linking, Biomedical Applications of Immobilized Enzymes and Proteins, vol. 1, 1977 (pp. 25-35).

*Primary Examiner*—David M. Nafe
*Attorney, Agent, or Firm*—Ostrolenk, Faber, Gerb & Soffen

[57] ABSTRACT

An immobilized enzyme product is produced by contacting an inert particulate support with an aqueous enzyme solution containing preferably at least 25% dissolved solids and with a water miscible organic solvent, and crosslinking the enzyme to insolubilize the enzyme on the support as a gel containing 50-90% water. The water miscible organic solvent is in substantial excess of the amount of water mixed with the support in the process. The solvent may be contacted with the support before or after contacting with the enzyme solution. The resultant immobilized enzyme product has a bulk volume 5 to 300% greater than the bulk volume of the support material. A least a portion of the gel is external to the support and constitutes at least 3% by volume of the immobilized enzyme product.

18 Claims, 4 Drawing Figures

500 micron  Fig. 1.
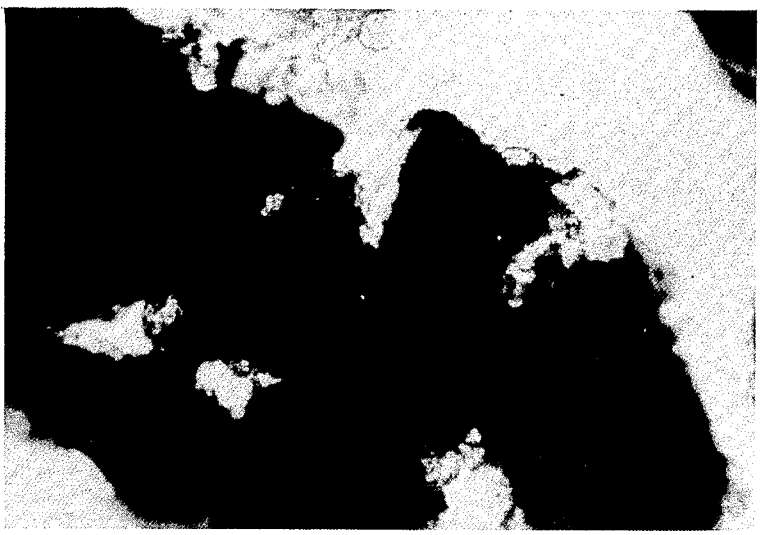
500 micron  Fig. 2.

500 micron

IMMOBILIZATION OF ENZYMES

This invention relates to immobilized enzymes.

Immobilization of enzymes on inert support materials is a potentially attractive way of utilizing enzymes for effecting chemical conversions on an industrial scale. Without immobilization, the enzyme is difficult to remove and is usually left in the product. Enzymes are expensive and immobilization offers the possibility of re-use of the enzyme with consequential savings. In particular, immobilization on particulate inert support material offers the possibility of fluidized bed operation or simple upflow operation, the usual inert support materials acting as a core of dense material and minimizing flow of the immobilized product in the substrate stream.

Physical and chemical methods are available for the immobilization of enzymes on inert support materials, especially on spheroids of glass, alumina or other inorganic material.

Examples of the physical methods include (i) adsorption of the enzyme on to the support surface and (ii) occlusion or entrapment of the enzyme within the support material, while examples of chemical methods include (iii) covalent coupling of the enzyme to the support surface and (iv) covalent cross-linking of the enzyme within pores of the support material.

Method (i), physical adsorption, preferably employs a porous support, thereby providing a greater surface area available for adsorption. Thus, for instance, U.K. Patent Specification No. 1,440,703 describes a method for converting glucose to fructose which employs an immobilized enzyme composite comprising glucose isomerase adsorbed within the pores of a porous alumina body having an average pore diameter of from 100 to 1000 Angstrom, this pore size permitting maximum loading of the enzyme in the pores.

Method (ii), physical entrapment, also employs a porous matrix within which the enzyme is immobilized. Various techniques are available for physical entrapment of the enzyme. For instance, U.K. Patent Specification No. 1,461,025 describes a method which involves adjusting the pH so as to vary the volume occupied by the molecules of an enzyme—the pH of an enzyme solution is initially adjusted to give a minimum or near-minimum enzyme volume, the solution admixed with a microporous carrier material, and the pH then adjusted to increase the volume of the enzyme, thereby entrapping the molecules in the micropores.

Method (iii), covalent coupling, typically involves using a reactive bifunctional coupling agent which can couple the enzyme molecules to the surface of the support material. Thus, as one example, U.K. Patent Specification No. 1,484,565 describes the coupling of enzymes or other biologically active macromolecules to the surface of support materials using diazotized m-diaminobenzene.

In an alternative procedure for covalent coupling, the surface of the support material is itself functionalized so as to be reactive with the enzyme. Thus, U.K. Patent Specification No. 1,412,563 describes a method in which a polymeric material is treated to generate free carboxylic acid groups which are then converted to reactive anhydride groups for subsequent reaction with the enzyme or other biologically active compound.

Finally, method (iv), covalent cross-linking, consists in intermolecular cross-linking of the enzyme after its adsorption on to the support material. For instance, U.K. Patent Specification No. 1,398,018 describes an insoluble enzyme composite which comprises a porous inorganic carrier and an enzyme adsorbed within the pores and inner surfaces of the carrier, the molecules of the adsorbed enzyme being cross-linked by a water-insoluble cross-linking agent. As the specification explains, the principal advantages of such a composite are that a greater amount of the pore volume it utilized for insolubilizing enzymes, proportionately less of the enzyme is exposed on the surface of the carrier, and a higher degree of enzyme immobilization is attained within the pores.

Of the methods (i) to (iv), the chemical methods (iii) and (iv) have met with greater favour because the enzyme is more securely united with the support material and is not solubilized during use. Physically adsorbed or entrapped substances are easily dislodged from the support, particularly if there is a change in the local environment, such as is associated with a change in pH, temperature or solvent.

In practice, the choice of chemical method and support material is often limited. To take one example, so far as we are aware, no one has as yet been able to take economic advantage of immobilization of amyloglucosidase, an enzyme widely used in the production of glucose from starch. Techniques and support materials are available for the immobilization, but their expense has usually proved too high.

The United Kingdom Atomic Energy Authority, UKAEA, have described in their U.K. Patent Specification No. 1,514,707 a method for immobilizing a biologically active substance, such as amyloglucosidase, in the pores of a porous support material. The method of UKAEA (as expressed by claim 1 of their patent) involves "introducing biologically active substance in to the pores of a porous support material and treating the biologically active substance to provide temporary retention thereof in the pores of the porous support material to hold the biologically active substance available in the said pores for cross-linking, and cross-linking the biologically active substance in the pores of the porous support material so as to immobilize biologically active substance in the pores of the porous support material".

As the Specification No. 1,514,707 explains, the invention utilizes the pores of a porous support material since, in this way, the surface area/volume ratio of the support material is greatly increased.

In common with the other methods which use porous support materials, the method of cross-linking the biologically active substance within the pores has, as a pre-requisite, the requirement that the pore size and pore structure of the porous support material should be such as to permit entry of the substance to be immobilized and eventual entry of species with which the immobilized substance reacts. In practice, this requirement means that only a few porous support materials can be used if one is hoping for efficient immobilization. Thus, whereas the Specification No. 1,514,707 mentions many inorganic and organic materials which can be used as the support, we find that in our hands the method of Specification No. 1,514,707 is unsatisfactory unless one is using certain glasses or titania spheroids which have been manufactured by carefully controlled processes in order to have a specific pore size. These materials with a controlled pore size are extremely expensive, to the point where it is usually not possible to take advantage of the potential savings offered by the immobilization technique.

As will be apparent from the foregoing discussion of the known techniques for immobilization of enzymes on inert support materials, it has previously been generally held that particularly for the chemical methods, immobilization of enzyme within pores of the support material was a key to success, the pores providing additional surface area for active enzymes.

Against this conventional thinking for the immobilization of enzymes on inert support materials, and in accordance with the present invention, we now provide a product where active immobilized enzyme is part of an external deposit on inert support material. The external deposit can take the form of an envelopping coating, or especially with particulate support material, the external deposit can be a discontinuous or irregular coating on individual masses of support material.

More particularly, but not exclusively, we provide an immobilized enzyme product comprising inert support material with an external deposit which contains immobilized enzyme and which forms at least 3% by volume of the product.

The external deposit attached to the inert support material and containing immobilized enzyme will usually form 10 to 75% of the product volume, more typically from 10 to 50% of the product volume. For the preferred products, the surface deposit ranges between 15 and 40% by volume of the product.

In addition, the deposit containing immobilized enzyme will usually contain more water than enzyme, and typically will be a gel. Suitable gels include those which comprise 50 to 95% water, more preferably 70 to 85% water (percentages being by weight), though as with the figures given for relative volume of the deposit the values can be varied as desired.

An external deposit which contains water in addition to immobilized enzyme has the advantage that diffusion of substrate through the material then becomes possible. In other words, the immobilized enzyme which can exhibit activity is not confined to those molecules which are outermost or otherwise exposed to substrate. A substrate-permeable external enzyme deposit is thus a beneficial feature of the invention. In effect, by using a gel deposit of immobilized enzyme on an inert support material it is possible to provide additional volume of active enzyme rather than additional area of active enzyme. For the present products, it is accordingly preferred that all or a major proportion of active enzyme is present in the external deposit: contrary to some expectations, it is possible to retain active enzyme on the outside of inert support material.

In accordance with our invention, we also provide a process for making immobilized enzyme products, which process comprises forming a gellable, external, enzyme-containing coating on support material by contacting the inert support material with an aqueous solution of the enzyme to be immobilized and with a water-miscible organic solvent, and contacting the externally coated support material with a cross-linking agent to gel the coating.

Optical microscopy of the various products which we have prepared by such a process shows that they comprise gel deposited on the inert support material. The cross-linked gel can usually be clearly seen as a complete or partial coating around the support, the gel normally having some transparency.

As will be apparent, the present process is not similar to the conventional prior art methods discussed in the introduction. Indeed, there is very little similarity with other proposals which do not immobilize enzyme on inert support material (and thus do not fall within the categories (i) to (iv) above) but which employ a gellable protein. The reader is referred, for instance, to U.S. Pat. No. 3,838,007, as well as to U.K. Pat. No. 1,571,987.

Briefly, in the U.S. patent a water-insoluble enzyme preparation is prepared by the steps of mixing a non-proteolytic enzyme with gelatin or fresh egg white, insolubilizing the mix to give particles by adding a water-immiscible organic solvent, treating the suspension to gel the gelatin (by cooling) or to gel the egg white (by heating), and cross-linking the gelled protein in particulate form to give a particulate product. It is readily apparent that the use of the water-immiscible solvent such as a higher alcohol renders in a particulate form the enzyme and gelling protein, and that this particulate form is maintained in subsequent steps. As a result of this particulate nature, it seems that no support material is required.

In the U.K. patent, amyloglucosidase or maltogenic α-amylase is coated on granular casein particles along with glutaraldehyde and egg albumen, so as to give a liquid-permeable, cross-linked enzyme/albumen coating to the casein particles. It is most significant to note that the U.K. Pat. No. 1,571,987 indicates on page 3 at lines 15 to 20 that the use of casein particles and the egg albumen is essential. It is said that attempts to use carrier materials of inorganic origin or of other proteins proved unsuccessful. This conclusion is reached after attempted direct cross-linking of the enzyme with glutaraldehyde, without the presence of a water-miscible organic solvent which is a feature of our process.

In the present process, support material which is inert is contacted with enzyme solution, water-miscible organic solvent and cross-linking agent so as to form an external, enzyme-containing gel deposit on the support material. The typical gel is relatively strong and shear-resistant, such that use of the product does not lead to rapid attrition of the deposit with loss in enzyme activity. Indeed, the active enzyme typically has long-term stability, with a half-life for the enzyme activity of more than 10 days being preferred.

A key to success with the present process is the formation, albeit sometimes transitorily, of a gellable coating on the inert support material. Such a coating can be formed in various ways, though our research has led us to employ an aqueous solution of the enzyme together with a water-miscible organic solvent. Using this system, there is little difficulty in forming a gellable coating after suitable experimentation by trial-and-error using routine procedures.

The order of the contacting of the support material with the enzyme solution, water-miscible solvent and cross-linking agent can be varied as desired, provided that ultimately the gel coating is obtained. For example, the inert support material can be contacted with the solvent and the enzyme solution added, followed by contacting with the cross-linking agent. As one alternative, the water-miscible solvent can be added with the cross-linking agent to inert support material which has been contacted with the enzyme solution.

The present invention makes use of an inert support material which is substantially inert to both unwanted physical and chemical effects which might occur during manufacture, storage or use of the present products.

Such a support material, for example, does not undergo dimensional changes upon contact with water. Equally, it is not susceptible to enzyme attack, as is possible particularly with proteolytic enzymes when immobilized on proteinaceous support material such as casein granules.

Given that it is inert, the nature of the support material is not critical. For inertness, it is much preferred that the support is not of polymeric organic material, and indeed the support material will usually be "inorganic", by which term we exclude the presence of organic compounds but include the possibility of a support containing elemental carbon. Preferably the support material consists of particles with dimensions of from 250 to 1500 micron. A maximum dimension less than about 150 micron is undesirable if the product is to be used in a fluidized bed reactor.

The present invention does not rely upon the presence of pores in the inert support material in order to obtain an active immobilized enzyme. Nevertheless, pores appear to be of some benefit in obtaining a more robust product in which the enzyme layer is less likely to break away.

Examples of support materials which can be used include particles of either naturally occurring or manufactured materials. For instance, we have performed satisfactory immobilizations using grains of river sand (with no porosity), particles of molachite (a naturally-occurring aluminosilicate with about 2% porosity), porous titania or hydroxyapatite spheroids (manufactured in accordance with the process described in U.K. Pat. No. 14,215,318 and with about 35% porosity) or particles of commercially available bone char (with about 30% porosity).

Bone char, otherwise known as bone black, bone charcoal or animal charcoal, is the preferred support material for the present invention. Bone char offers a combination of advantageous properties which is not met by the materials which have previously been suggested for use as support material, these advantages being particularly brought out in a product in accordance with the present invention.

Bone char is obtained at an economically favourable cost from a naturally-occurring raw material, and consists principally of a hydroxyapatite structure over which there is a thin, evenly-dispersed coating of active carbon, with the particles being of an irregular form and providing a suitable 'key' for adhesion of the external deposit. In addition, it has been used for many years in sugar refining throughout the world, and it is well established that its use entails no hazardous problems in the food industry. It exhibits a good degree of thermal stability and ordinarily contains no artificial additives which might give rise to further problems even when used in midly acidic conditions.

The particle size of the bone char is not critical for a successful immobilization. We prefer to use particles with a minimum dimension of less than 2 mm, more preferably less than 1 mm, and with a maximum dimension of less than 6 mm, more preferably less than 2 mm.

In contacting the support material with the enzyme solution, it is preferred to use an excess of the solution so that the support material is loaded to saturation with the enzyme. At the least, with a porous material it is necessary to use sufficient enzyme solution to ensure that enzyme is available on the outside of the support material for forming the external coating.

It is difficult to give figures for the amount of enzyme to be used which are applicable for all the available support materials, especially since some enzyme may be soaked up into the pores of a porous support material. If desired, one can determine the amount of enzyme solution which will be taken up by the pores, and then ensure that excess solution over the amount required for the pores is added. One convenient way for determining the amount taken up by the pores is to soak the support material in excess solution and then drain off the solution, preferably by suction. Weighing the support material before and after will then give a reasonable approximation of the weight of solution taken up by the pores in the presence of excess solution.

With non-porous materials such as grains of sand, it is currently preferred to use a solution containing from 1 to 25 g of dry weight enzyme preparation per 100 ml of support material, more preferably 4 to 20 g enzyme preparation per 100 ml support material and particularly 5 to 15 g per 100 ml. These ranges seem also to be suitable for materials with limited porosity (up to 10% porosity by volume), and can be used to give a guide to the amount of excess enzyme solution required for a surface coating of porous materials after the pores have been filled.

For very porous support materials such as bone char it is currently preferred to use a solution containing from 5 to 70 g, more preferably 15 to 40 g, of dry weight enzyme preparation per 100 ml of support material and particularly 15 to 25 g per 100 ml. These ranges seem also to be suitable for other materials with above 10% porosity. In general with porous materials, the present process employs greater weights of enzyme preparation per unit volume of support material than have previously been employed.

In order to aid formation of the gellable coating, the present process also often employs enzyme solutions of higher concentration than have previously been employed for physical or chemical immobilizations. Solutions of 15 to 20% solids have typically been used in the past, whereas the present process is preferably founded on the use of an enzyme solution containing at least 25% solids, more preferably at least 35% solids.

Enzyme solutions containing at least 25% solids have appreciable viscosity, and it is possible that this is a factor in obtaining good formation of the gellable coating. Moreover, as a preliminary test when considering suitability of an enzyme solution, it is noticeable that such solutions normally do not give with a water-miscible solvent a particulate or other precipitated product. Instead, they give a putty-like or other plastic mass, though this test is not conclusive since other variables in the process will ultimately determine suitability.

The preferred concentration range is 35 to 60% solids, though higher concentrations can be employed provided that the solids are in solution.

While we have particularly developed our process for use in immobilization of amyloglucosidase, the nature of the enzyme is not critical. The process is particularly suited for saccharifying enzymes, including not only amyloglucosidase but also amylases. However, and more generally, the present process can be used, for example, with oxido-reductases, transferases, hydrolases, lyases, isomerases and lyases. The process can readily employ commercially available enzyme preparations; although preparation of a concentrated solution is usually necessary, it is ordinarily unnecessary to purify the enzyme. Indeed, the presence of conventional stabilizers may be of advantage.

The enzyme solution is an aqueous one, and preferably contains from 10 to 70% by weight of water, for example 35 to 60% water. More importantly, the enzyme solution preferably does not contain other added materials, and in particular it should not contain any insolubilising agents for protein. The formation of a gellable coating of the enzyme on the support material appears to involve loading the support material with enzyme which has not been irreversibly precipitated.

The formation of the gellable coating in the present process is further predicated on the presence of a water-miscible solvent. Acetone offers many advantages, particularly in price and in the ease with which it may be recovered for subsequent use, and is the preferred water-miscible solvent. However, the use of acetone is not essential and other ketones or other classes of water-miscible solvents such as lower alcohols, for instance ethanol, may be employed.

As mentioned above, there are two preferred ways in which the support material is contacted with the water miscible solvent. In the most preferred way, the support material is mixed with the solvent and then the enzyme solution is added. In the alternative preferred way, the support material is first contacted with the enzyme solution, and then the solvent is added, preferably in admixture with the cross-linking agent being employed to gel the gellable coating.

We are uncertain of the precise role played by the acetone or other water-miscible solvent and how it helps the formation of a gellable coating on the outside of the inert support material. At the least, it is clear that the solvent does not serve to form a conventional precipitate of the enzyme. Instead, in our process the solvent encourages the formation of the gellable coating, maintaining the enzyme in a soluble or quasi-soluble form which upon cross-linking gives a gel and not a true precipitate.

It is believed that as part of its action, the solvent helps to modify the water content of the enzyme solution in the locality of the surface of the support material. In the most preferred process, involving contact of the support material with the water-immiscible solvent, addition of the aqueous enzyme solution and then contacting with cross-linking agent, it is apparent that it is beneficial to replace the organic solvent during addition of the enzyme solution, thereby removing water from the system.

The amount of solvent will ordinarily exceed the total amount of water added to the system, with a ratio of solvent to water above 2:1 and especially from 3:1 to 5:1 being preferred. The required amount of solvent will usually be found by trial-and-error, since it is dependent upon other variables. Thus, optimum values cannot be recited which will apply in all instances.

During or after the formation of a gellable coating on the outside of the inert support material, a cross-linking agent is employed to form a gel on the support material. The preferred agent is glutaraldehyde, especially 50% aqueous solution of glutaraldehyde. Other known cross-linking agents selected from those given in the Patent Specifications considered earlier can be used.

The cross-linking agent is preferably used in relatively low amounts in order to avoid undue hardening of the gel. For glutaraldehyde, a weight ratio of glutaraldehyde to enzyme of from 1:3 to 3:1 is particularly convenient.

The use of the cross-linking agent leads to the desired product wherein the inert support material is coated with the enzyme-containing gel. Particularly if there is no agitation during the gel-forming step, the product may have a continuous gel phase acting as a matrix enclosing the support material. Such a product may be broken down in size giving a product in which the gel deposit is an irregular coating, the irregularities arising from shearing of the gel. Better still, with a particulate support material the formation of a gel matrix can be largely or completely avoided by agitation during cross-linking: gentle tumbling is the preferred mode of agitation. In some circumstances, it may be desired to maintain the gel matrix—such products are also part of the subject of this invention.

After the cross-linking step, the resultant product is preferably washed with water to remove any excess of the various reagents.

The process of the present invention gives a product which has an appreciably greater volume than the initial support material used in its preparation. Typically the product volume is from 5 to 300%, more often 10 to 100% greater, than that of the support material itself, with an increase of 20 to 60% being preferred. While these volume increases can be calculated on the basis of the actual volume of the support material, it is for most purposes a practical simplification to relate them to the bulk volume of the support material.

The products of this invention can then be used to effect enzyme-mediated conversions of substrates. The immobilized enzyme can be used in a manner similar to other immobilized systems, and can for example be placed in a reactor vessel, such as a column, through which the substrate can be passed in the form of a solution, with upward passage through a column being preferred.

Before giving Examples illustrative of the invention, we consider in more detail the techniques which we have developed for immobilization of amyloglucosidase as a gel on inert support material. Amyloglucosidase is preferably immobilized in accordance with the present invention by using one of two procedures as follows:

Procedure A: "Rotary Method"

(I) Particles of virgin bone char are washed with dilute hydrochloric acid until the char no longer exhibits a buffering action against the acid. The char is washed to remove any adherent acid and is then suspended in a volumetric excess of acetone, preferably a 3-fold excess or thereabouts. The resultant slurry is gently agitated by rotation, and is ready for addition of the enzyme solution as a concentrated solution.

(II) We employ the amyloglucosidase preparation available from ABM Industrial Products Limited of Stockport, England. The aqueous amyloglucosidase solution as obtained from ABM typically contains around 20% by weight of solids, and we prefer first to evaporate off some of the water to raise the enzyme concentration. Suitably the solids concentration is raised to at least 40% by weight, and conveniently, about 20 g or more of the enzyme preparation (as dry solids) is used for every 100 ml of the bone char. The enzyme solution is best added slowly, and possibly with intermittent replacement of the acetone as it takes up water from the enzyme solution.

(III) Any excess liquid is drained from the bone char after the step (II). The particles are then optionally washed with acetone. At this stage, it is apparent that an external coating has formed on the bone char particles: the particles are tacky and tend to adhere together.

(IV) The enzyme coating is then cross-linked using glutaraldehyde or some other cross-linking agent. Our best results with the Rotary Method have been obtained using an aqueous solution of 50% glutaraldehyde, to which some water may be added particularly if the initial enzyme solution had a high solids content (and thus a low water content). Tannic acid is not added to the glutaraldehyde. The glutaraldehyde to enzyme ratio is preferably set at 2:3. After further rotation, the product is washed with water. It is then largely particulate, though with some agglomeration: formation of a gel coating is apparent. Sieving or other procedure can be used to break down the agglomerates.

Procedure B: "Slurry Tank Method"

(I) Acid washed bone char prepared as for the rotary method is contacted with an about equal volume of concentrated enzyme solution. Suitably around 50 g of enzyme solids is present for every 100 ml of bone char.

(II) The coated bone char is then added dropwise to a stirred mixture of acetone and 50% aqueous glutaraldehyde. The acetone will be the main component of the liquid, with an acetone: 50% glutaraldehyde ratio of about 6:1 being convenient. The glutaraldehyde is preferably employed at about half the weight of enzyme solids added at step (I). Stirring during this step (II) helps to give a particulate product, though some sieving may be needed if individual gel-coated particles are especially desired.

Such a process embodying the steps (I) to (IV) or (I) and (II) can be effected on a large scale in an economically favourable manner; acid washed bone char is about 1/10th the price of the special glass or titania spheroids which are best for the immobilization process developed by UKAEA. Our costings suggest that for the first time we have an economically advantageous method of immobilizing amyloglucosidase for use on an industrial scale.

The present invention is illustrated by the following non-limiting examples. In the Examples, reference is made to the accompanying drawings in which:

FIG. 1 is a photograph taken through a microscope by transmitted light of the bone char particles employed as support material in Example 1;

FIG. 2 is a photograph taken as for FIG. 1 of the particulate product obtained in Example 1;

EXAMPLE 1

Amyloglucosidase was immobilized on bone char and the nature of the product determined. A laboratory scale procedure was used which was substantially the same as the "Slurry Tank Method" given above, except that at step (II) the mixture of acetone and glutaraldehyde was added dropwise to the coated bone char.

(i) Preparation

An aqueous amyloglucosidase solution obtained from ABM Industrial Products Limited was concentrated to 40% solids by weight. 78 g (69 ml) of the 40% enzyme solution was mixed in a beaker with 100 ml (80 g) of acid-washed bone char having a mesh size between 500 and 1000 micron. The soluton was present in considerable excess over the volume required to fill the pores of the bone char.

150 ml of a mixture of 124 ml of acetone and 26 ml of 50% aqueous glutaraldehyde was added dropwise to the bone char. The resultant mix was stirred for 10 seconds, and then left for one hour.

In this way, a block product was obtained comprising a mass of gel throughout which were dispersed the bone char particles: the block had assumed the shape of the beaker in which the experiment had been carried out.

The block product was washed with water and then broken up by forced passage through a 2000 micron sieve, giving 197 ml of a particulate product comprising bone char particles with a gel deposit of amyloglucosidase.

(ii) Microscopy

Figure 3:
FIG. 3 is a photograph taken through a microscope by reflected light of the particulate product obtained in Example 1.

Reference is now made to FIGS. 1 to 3 of the drawings.

FIG. 1 is a photograph taken through an optical microscope of the bone char used in this experiment. In this instance, transmitted light is employed (i.e. the light is coming from behing the particles). It will be seen that the particles have an irregular but clearly defined surface.

FIG. 2 is a photograph also by transmitted light and at the same magnification of the particulate product obtained in this experiment. The dark particles can still be seen, but clearly these are attached to them deposits of the gel material.

The presence of the deposited gel is also apparent from FIG. 3, which is a photograph of the same product taken at the same magnification as for FIGS. 1 and 2. However, in this instance, reflected light is employed (i.e. the light is coming from in front of the particles). The gel can clearly be seen as rounded light-reflecting areas. The bone char itself has very poor light reflecting properties, and an attempt to photograph the bone char itself by reflected light gave a uniformly black picture with no apparent features.

(iii) Properties

The enzyme activity of the particulate product was assayed by a standardized procedure. A trial column was filled using the product and assayed for its ability to raise the DE of a glucose syrup, DE being the amount of reducing sugar which is present when determined as dextrose and calculated as a percentage of the dry weight. A 42 DE acid-thinned syrup at pH 4.5, 55° C. and 40% solids was passed down the column at variious flow rates (measured in empty column volumes per hour, ecv/h) and the percent dextrose of the issuing syrup was determined.

A syrup of about 81.3% dextrose was obtained at a flow rate of 10 ecv/h, while at 12 ecv/h the product was 80% dextrose syrup.

EXAMPLE 2

Example 1 was repeated using 66 ml of of 50% enzyme solution instead of the 69 ml of 40% enzyme solution. A block product was obtained in the same way, though it was noticeably more resistant to shear. After sieving, 223 ml of particulate product was obtained.

Upon assay by the same procedure, the 42 DE syrup was converted to 80% dextrose syrup at 10 ecv/h and to 78.2% dextrose syrup at 12 ecv/h.

EXAMPLES 3 and 4

Example 1 was repeated using either 76 ml of 61% enzyme solution (Example 3) or 72 ml of 30.5% solution (Example 4). Respectively, the resultant particulate product had a volume of 292 ml or 129 ml.

Upon assay by the same procedure, the product of Example 3 gave 76 DE syrup at 30 ecv/h and 73.4 DE syrup at 12 ecv/h.

The product of Example 4 gave 78.2% dextrose syrup at 10 ecv/h and 76.7% dextrose syrup at 12 ecv/h.

COMPARATIVE EXAMPLE 1

A particulate product was produced from the amyloglucosidase employed in the previous examples using the best procedure we know based on the method as described in UK Pat. No. 1514707.

25 ml of 17% enzyme solution was added at 4° C. to 100 ml of titania spheroids. 60 ml of cooled immobilization liquor containing 1 g tannic acid (enzyme precipitant) and 9 g of glutaraldehyde was stirred in and the immobilized allowed to proceed for five hours.

The resultant product was particulate.

After washing, the product was assayed in the same way as in the previous examples. At 10 ecv/h, a syrup of 67.2% dextrose was produced. At 12 ecv/h, the product was 61.6% dextrose. A flow rate of only 5 ecv/h was required to produce 81.3% dextrose syrup (compare Example 1, where 81.3% dextrose syrup was obtained at 10 ecv/h).

COMPARATIVE EXAMPLE 2

The procedure of Comparative Example 1 was repeated but using 100 ml of bone char as the support material.

The resultant product was again particulate.

Upon assay, a 61.7% dextrose syrup was obtained at 10 ecv/h, and a 56.5% dextrose syrup at 12 ecv/h. At 5 ecv/h the product gave a 74.7% dextrose syrup.

EXAMPLE 5

Example 1 was repeated using formaldehyde in place of the glutaraldehyde.

From the resultant product, 78% dextrose syrup was produced at 4.6 ecv/h from 42 DE syrup.

EXAMPLE 6

Amyloglucosidase was immobilized by the Rotary Method. 5 kg of acid washed bone char (500–1000 micron) was suspended in 20 l of acetone and rotated in a large blender. 2.5 kg of 60% solids amyloglucosidase was pumped in over 50 minutes. Thereafter, 7 l of wet aceton was removed and 4 kg of 50% glutaraldehyde added along with 1.75 kg of water. The mixture was rotated for 2 hours and then water-washed, giving a mainly particulate product with some agglomeration. The product was passed through a 2000 micron sieve before use.

The stability of enzyme in the product was determined as a half-life. 300 ml of the product was loaded in a column and used at 60° C. to convert 42 DE syrup to 88 DE syrup on a continuous basis. At weekly intervals, the flow rate required to give 88 DE syrup was recorded. As the experiment proceeded, the flow rate for 88 DE syrup decreased.

From the results, and using conventional half-life mathematics, it was calculated that the enzyme activity in the product had a half-life of 40 days.

The same half-life of 40 days was found for a product produced by the Slurry Tank Method.

EXAMPLE 7

The slurry tank method was used to immobilize other enzymes.

(a) Dextranase 70 g of 20% solids dextranase was mixed with 74 g of bone char, and 48 g of 50% glularaldehyde made up to 200 ml with acetone was added. After 1.5 h, the product was washed and broken up.

The product column was 110 ml. It was assayed using 5% dextran solution at pH 5.0 and 55° C. Just over 20% combined dextrose, maltose and triose was produced at 3.6 ecv/h.

(b) Fungal α-amylase 200 g of Fungamyl 800L from Novo Industries was added to 400 g of bone char. A mix of 60 g/l, 50% glutaraldehyde in acetone was added and the immobilization allowed to proceed for 1.5 h. After washing, 850 ml of product was obtained which was sieved and then ready for use.

42 DE acid-thinned syrup was converted at pH 6.0, 40% solids and 50° C., giving 30% maltose at 18 ecv/h.

(c) Bacterial α-amylase 100 g of BanL 120 from Novo Industries was stirred into 200 g of bone char. 60 g/l 50% glutaraldehyde in acetone was added and the mixture left for 1.5 h.

The product after washing and sieving was assayed at pH 6.0 and 55° C. using an enzyme-thinned syrup containing 75% of oligosaccharides having a degree of polymerisation above 3 ($DP_3$). At a flow rate of 3.9 ecv/h, the syrup was converted to a product with 45% oligosaccharides above $DP_3$.

(d) Pullulanase 100 g of pullulanase solution obtained from ABM Chemicals Ltd. was added to 200 g of bone char. 60 g/l, 50% glutaraldehyde in acetone was added and the mix left for 1.5 h.

After washing and sieving, the product was assayed using 13% beer wort containing 22.5% oligosaccharides above $DP_4$. At 55° C., pH 6.0 and 20 ecv/h, the wort was converted to a product containing 15% oligosaccharides above $DP_4$.

(e) Lactose 45 g of Sumylact, a β-D-galactosidase from *Aspergillus oryzae* was dissolved in 40 g of water and stirred with 60 g of bone char. 15 ml of 33% glutaraldehyde was dissolved in 185 ml acetone and added. The immobilization was allowed to proceed for 1.5 h.

After washing, the product has a volume of 175 ml. It was assayed against 11% reconstituted whey at pH 5.0 and 50° C. At 0.45 kg of whey solids per liter of enzyme product per hour, a syrup containing 10% residual lactose was produced.

(f) Invertase 80 g of invertase solution containing glycerol (refractive index 1.408) was added to 74 g of bone char and then the bone char was washed with three batches of 200 ml acetone. 50% glutaraldehyde made up to 240 g/l with acetone was added, the mix stirred for 10 seconds, and then left for 1 h.

After washing and sieving, the product was assayed against 40% solids sucrose solution at pH 6.5 and 40° C. At 2.4 ecv/h, the sucrose was converted to 45% glucose, 45% fructose and 6% sucrose, while at 6.6 ecv/h the sucrose gave 30% glucose, 30% fructose and 30% sucrose.

EXAMPLE 8

A series of immobilizations of amyloglucosidase on different support materials was carried out using a procedure based on that of Example 1.

The immobilizations were effected using 40% solids enzyme and 100 ml samples of three different supports in the particle size range 425 to 600 micron. Acid washed bone char and titania particles represented supports with pores, while sand was employed as a poreless support. Several immobilizations were performed on each support over a range of enzyme loadings, up to the maximum possible. This maximum was around 70 ml for supports with pores and 40 ml for poreless supports.

The immobilized products were water-washed and pressed through an 850 micron sieve to give individual particles. The final volumes were measured.

Figure 4:
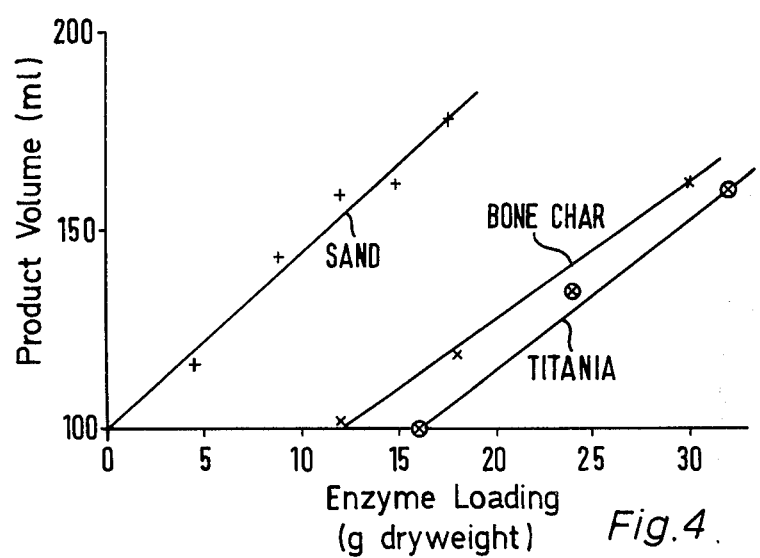
FIG. 4 is a graph of volume increase against enzyme loading for various support materials, and is referred to in Example 8.

Reference is now made to FIG. 4, in which the volume of the product is plotted against the amount of added enzyme. Bearing in mind that 100 ml of support material was used each time, it is seen that with sand there is always a greater product volume, indicative of gel formation.

On the other hand, with the porous support materials there is no volume increase until a certain amount of enzyme (12 g for bone char, 16 g for titania) has been added. Thereafter, there is a progressive increase in volume of the product with increase in enzyme amount.

The results shown in FIG. 4 can readily be explained on the basis that the pores in the bone char take up 30 ml of the enzyme solution (i.e. 12 g solids), while the titania takes up 40 ml of the solution; for sand there are no pores to be filled. Once pores where present have been filled, all three support materials act in a similar manner and give a similar relationship between enzyme loading and volume increase.

The enzyme activity was assessed against 42 DE syrup, though in this instance the flow rate required to produce 79% dextrose syrup was determined using products which had shown a volume increase of about 60 ml above the original support volume of 100 ml.

A bone char product of final volume 163 ml, prepared using 30 g of enzyme, gave 79% dextrose syrup at 7.4 ecv/h. A titania product of final volume 160 ml and prepared 32 g of enzyme gave the 79% dextrose syrup at 7.2 ecv/h. A sand product of final volume 162 ml and prepared from 15 g of enzyme gave the desired syrup at 7.0 ecv/h.

These results clearly indicate that the enzyme immobilized in the pores plays little if any role in converting the 42 DE syrup to 79% dextrose syrup.

In contrast, maximum loading of enzyme into the pores but not externally gave markedly different results. Using 12 g or 16 g enzyme for 100 ml of bone char or titania, respectively, the final product had a volume of substantially 100 ml. 79% dextrose syrup was then obtained at 4.9 ecv/h from the bone char product and at 5.8 ecv/h from the titania product. These flow rates are respectively about 60% and about 80% of the flow rates measured for the products of the invention having the final volume of 160 ml.

The moisture content of the gel deposit was assessed by repeating an experiment which led to a product volume of 160 ml but with omission of the support material. This procedure gave a block of the gel itself, density 1.02 g/ml, and water content 80%. Repitition using 60% enzyme solution gave a block with a water content of 72%. After enforced passage through a mesh, the gels exhibited the ability to convert 42 DE syrup. Prolonged operation was difficult; a fluidized bed was not possible since the gel had a similar density to the syrup.

What we claim is:

1. An immobilized enzyme product consisting essentially of particulate inert bone char carrying an immobilized crosslinked enzyme in the form of a gel, said gel consisting essentially of active immobilized enzyme and 50–90% water, at least a portion of said gel being external to said bone char and said portion forming at least 3% by volume of said product, the bulk volume of said product being from 5 to 300% greater than the bulk volume of said bone char.

2. A process for making an immobilized enzyme product, which process consists essentially of mixing a water miscible organic solvent with an inert insoluble solid particulate support material, mixing the resultant mixture with an aqueous solution of enzyme containing at least 25% dissolved solids consisting essentially of enzyme preparation solids in an amount sufficient to load the support material to saturation with the enzyme, and thereafter contacting the enzyme loaded support material with an amount of crosslinking agent sufficient to crosslink and insolubilize the enzyme on the support material as a gel containing 50–90% water to form said immobilized enzyme product, said solvent being present in substantial excess of the total amount of water mixed with said support material in the process, at least 3% by volume of said gel being external to said support material, and the bulk volume of said immobilized enzyme product being 5 to 300% greater than the bulk volume of said support material.

3. A process for making an immobilized enzyme product, which process consists essentially of mixing an inert insoluble solid particulate support material with an aqueous solution containing at least 25% dissolved solids consisting essentially of enzyme preparation solids in an amount sufficient to load the support material to saturation with the enzyme, and thereafter contacting the enzyme loaded support material with a water miscible organic solvent in combination with an amount of crosslinking agent sufficient to crosslink and insolubilize the enzyme on the support material as a gel containing 50–90% water to form said immobilized enzyme product, said solvent being present in substantial excess of the total amount of water mixed with said support material in the process, at least 3% by volume of said gel being external to said support material, and the bulk volume of said immobilized enzyme product being 5 to 300% greater than the bulk volume of said support.

4. The process of claim 2 or 3 wherein said enzyme is a saccarifying enzyme.

5. The process of claim 4 wherein the enzyme is amyloglucosidase.

6. The process of claim 2 or 3 wherein the water-miscible organic solvent is a ketone or lower alcohol.

7. The process of claim 6 wherein the water-miscible organic solvent is acetone.

8. The process of claim 2 or 3, wherein the aqueous solution of the enzyme contains 35–60% solids.

9. An immobilized enzyme product produced by the process of claim 2 or 3.

10. The product of claim 9, wherein said external gel forms a continuous matrix enclosing said support material.

11. The product according to claim 9, wherein said external gel is a discontinuous, irregular coating on said particulate support material.

12. The product of claim 11, wherein said support material is particulate bone char.

13. The product of claim 9, wherein said enzyme is a saccharifying enzyme.

14. The product of claim 9, wherein said external gel is 10 to 75% of the product volume.

15. The product of claim 7, where the external gel contains 70 to 85% water.

16. The product of claim 1, wherein said enzyme is amyloglucosidase.

17. An immobilized enzyme product of claim 9, wherein the bulk volume of said product is 10-100% greater than the bulk volume of said support material.

18. A method for conversion of a substrate by an enzyme source, wherein said immobilized enzyme product of claim 9 is employed as said enzyme source.

* * * * *